United States Patent

Kleiner

[11] Patent Number: 4,904,813
[45] Date of Patent: Feb. 27, 1990

[54] CYANOMETHYL ACID HALIDES OF PHOSPHORUS AND PROCESS FOR THEIR PREPARATION

[75] Inventor: Hans-Jerg Kleiner, Kronberg/Taunus, Fed. Rep. of Germany

[73] Assignee: Hoechst Akteingesellschaft, Frankfurt am Main, Fed. Rep. of Germany

[21] Appl. No.: 165,581

[22] Filed: Mar. 8, 1988

[30] Foreign Application Priority Data

Mar. 10, 1987 [DE] Fed. Rep. of Germany ....... 3707639

[51] Int. Cl.$^4$ ............................................ C07C 121/00
[52] U.S. Cl. ..................................................... 558/386
[58] Field of Search ......................................... 558/386

[56] References Cited

U.S. PATENT DOCUMENTS 4,120,688 10/1978 Otten .................................... 558/386

OTHER PUBLICATIONS

R. I. Bystrova et al., *Zh. Obsh. Khim.* 29:2057–2060 (1959) (Eng. lang. ed'n).

Primary Examiner—Mary C. Lee
Assistant Examiner—J. Richter

[57] ABSTRACT

The invention relates to compounds of the general formula

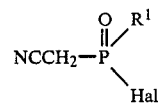

in which $R^1$ represents Hal or $C_1$–$C_3$-alkyl and Hal reprsents a halogen having an atomic weight of 35 to 80.

The invention also relates to a process for the preparation of such compounds by reacting a compound of the general formula II

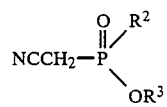

in which $R^2$ represents $C_1$–$C_3$-alkyl or $OR^3$ and $R^3$ represents $C_1$–$C_8$-alkyl, preferably $C_1$–$C_3$alkyl, with an acid chloride of the formula $MHaL_2$ (III), in which M represents SO, CO or $PHal_3$ and Hal represents a halogen having an atomic weight from 35 to 80, and in which the reaction, if M is Co, is carried out in the presence of a catalyst which is customary for the phosgenation of diesters of phosphonic acid.

Finally the invention relates to alkyl esters of cyanomethyl-methylphosphinic acid, i.e. to products of the formula II in which $R^2$ is a methyl group and $R^3$ is an alkyl group of 1 to 6 carbon atoms.

12 Claims, No Drawings

CYANOMETHYL ACID HALIDES OF PHOSPHORUS AND PROCESS FOR THEIR PREPARATION

DESCRIPTION

Cyanomethyl acid halides of phosphorus, process for their preparation and their precursors, alkyl esters of cyanomethyl-methylphosphinic acid The invention relates to cyanomethyl acid halides of phosphorus, a process for their preparation and their precursor ethyl cyanomethyl-methylphosphinate. The invention relates in particlar to cyanomethylphosphonic acid dichloride and alkyl-cyanomethylphosphinic acid chlorides.

Up to now the preparation of cyanomethylphosphonic acid dichloride has not been successful. Oxidative chlorophosphorylation of acetonitrile only resulted in the formation of phosphoryl chloride. Small amounts of a higher-boiling substance of a boiling point of about 70° C./0.4 kPa which decomposed during distillation with the formation of phosphoryl chloride and acetonitrile were obtained (R.J. Bystrova et al., Zh. Obsch. Khim 29, 2057 (1959) English).

The invention provides compounds of the general formula I (see Patent claim 1) in which $R^1$ represents Hal or $C_1$–$C_3$-alkyl, but is preferably methyl, and Hal is a halogen having an atomic weight of 35 to 80. Here cyanomethylphosphonic acid dichloride and cyanomethyl-methylphosphinic acid chloride are preferred. These compounds are stable even at temperatures of 100° C. or more, unlike the known products described in the abovementioned reference.

The cyanomethyl halides mentioned can be prepared in good yields from the corresponding cyanomethyl esters of the general formula II (see Patent claim 6) in which $R^2$ represents $C_1$–$C_3$alkyl or $OR^3$ and $R^3$ represents $C_1$–$C_8$-alkyl, preferably $C_1$–$C_3$-alkyl, by reaction with acid halides of the general formula $XHAL_2$ (III) in which X represents SO, CO or $PHal_3$ and Hal represents bromine or preferably chlorine. If phosgene or the corresponding bromine compound is used as the acid halide X=CO) in this reaction, it is necessary to use catalysts as customary for the phosgenation of diesters of phosphonic acid. Such catalysts can also be used for the reaction with thionyl halide. Examples of suitable catalysts are A. tertiary aliphatic and aromatic amines and phosphines, such as trimethylamine, triethylamine, the various tripropyl- and tributylamines, triphenylamine, trimethylphosphine, triethylphosphine, the various tripropyl- and tributylphosphines and/or B. quaternary ammonium salts or phosphonium salts, such as tetramethylammonium chloride or bromide and/or C. heterocyclic compounds of aromatic character, such as pyridine and 4-(dimethylamino)-pyridine and/or D. Other nitrogen or phosphorus compounds with a valency of the N or P atom higher than 3, such as pyridine N-oxide, trimethylphosphine oxide, tributylphosphine oxide, trihexylphosphine oxide, triphenylphosphine oxide.

All catalysts are used in amounts of at least 0.01 percent by weight, for example up to 5% by weight or more, based on compound II. Amounts of 0.5 to 2 percent by weight are preferred. They can be used as such, if desired as their salts, in particular as their hydrochlorides. Solvents which are suitable as reaction medium are those which are inert towards the reaction participants under the reaction conditions, such as dichloromethane, toluene and chlorinated aromatic hydrocarbons such as chlorobenzene. However, it is preferable not to use any solvent.

The temperatures which are applied in the process are dependent on the type of acid chloride used. If phosphorus pentahalide is used, for example the pentachloride, the reaction is generally carried out at −10° to +100° C., preferably at 20° to 80° C. If thionyl chloride or phosgene are used, the reaction is in general carried out at 70° to 150° C., preferably at 80° to 110° C.

The reaction can also be carried out at a higher pressure than atmospheric pressure. This is particularly of interest if phosgene or thionyl chloride are used. However, as a general principle, reactions at atmospheric pressure are preferred. For practical purposes, the reaction is carried out in such a manner that the acid halide is metered into the phosphonic or phosphinic ester, in portions or continuously. Sometimes it is advisable not to add the catalyst or further amounts thereof until a later stage of the reaction, after the reaction has subsided.

Vigorous mixing is advantageous, especially when gaseous phosgene is used. After the reaction has ended, the reaction product is isolated, for example by distllation.

Suitable examples of alkyl groups of 1 to 3 carbon atoms are methyl but also ethyl, propyl and isopropyl; however, methyl is preferred. Suitable examples of alkyl groups of 4 to 8 carbon atoms are the various butyl, pentyl, hexyl, heptyl and octyl groups, for example the n-, sec.-, tert.- or isobutyl radical or the 2-ethylhexyl radical.

Most starting materials are known; some, such as those alkyl esters of cyanomethyl-methylphosphinic acid in which the alkyl radical contains 1 to 6 carbon atoms, for example the ethyl ester according to Example 2, are new. Examples of alkyl radicals are methyl, ethyl, and one of the various propyl, butyl, pentyl and hexyl radicals. Radicals of 2 to 4 carbon atoms and in particular the ethyl radicals are preferred. The esters which are homologous to the ethyl ester can be prepared from the homologous dialkyl esters of methylphosphonic acid by a procedure analogous to Example 2. These compounds are also provided by the invention The acid halides prepared by the process according to the invention are valuable intermediates, for example for the preparation of aminocarbonylmethyl phosphonic acid and alkyl-aminocarbonylmethylphosphinic acids, the preparation of which has been described in copending patent application P 37 07 638.8 corresponding to U.S. application Ser. No. 165,534, filed of even-date herewith, abandoned in favor of a continuation thereof, U.S. application Ser. No. 262,110, filed Oct. 19, 1988.

EXAMPLES

1. - Cyanomethylphosphonic acid dichloride 480 g (2.71 mol) ofdiethyl cyanomethylphosphonate were mixed with 3.6 g of triphenylphosphine and heated to 85° C. With vigorous stirring, phosgene was introduced over a period of 14 hours. Excess phosgene was then removed under reduced pressure. The mixture was then distilled at 0.067 kPa. 390 g of cyanomethylphosphonic acid dichloride passed over at a temperature of 94° to 97° C. This corresponds to a yield of 91% of theory.

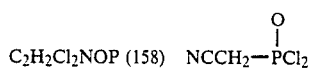

C$_2$H$_2$Cl$_2$NOP (158)

calculated: 15.19% C; 1.27% H; 44.94% Cl; 8.86% N; 19.62% P; found: 15.5% C; 1.2 % H; 43.6 % Cl; 8.8 % N; 19.1% P.

2. - Cyanomethyl-methylphosphinic acid chloride (a) Ethyl cyanomethyl-methylphosphinate 226.5 g (3 mol) of chloroacetonitrile were heated to 60° C. 470 g (3.53 mol) of diethyl methylphosphonate were added dropwise over a period of 3 hours at 70° to 80° C. During this step heating was not necessary; the reaction was exothermic. Ethyl chloride was collected in a down-stream cold trap. After the dropwise addition was finished, the mixture was slowly heated to 125° C. and kept at this temperature until no more waste gas (ethyl chloride) could be detected. The mixture was subsequently cooled and distilled through a column under an aspirator vacuum to give 418 g of ethyl cyano-methtylmethylphosphinate (b.p. 108°-109° C., 0.0133 kPa). This correspnds to a yield of 95% of theory, based on the amount of chloroacetonitrile used.

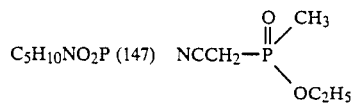

C$_5$H$_{10}$NO$_2$P (147)

(b) Reaction according to the invention

Over a period of 4 phosgene was introduced into 200 g (1.36 mol) of ethyl cyanomethyl-methylphosphinate at 100° C. with vigorous stirring. 1 g of 4-(dimethylamino)-pyridine was then added. Over the course of a further 3 hours phosgene was introduced again. Excess phosgene was then removed under an aspirator vacuum. The resulting reaction mixture was distilled at 0.067 kPa and at a bath temperature of 140° C. by means of a thinfilm evaporator to give 160 g of cyanomethyl-methylphosphinic acid chloride. This corresponds to a yield of about 85% of theory. The product was then distillable by a normal vacuum distillation (b.p. 117°-123° C., 0.053 kPa).

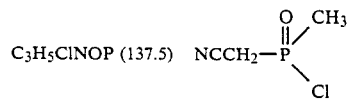

C$_3$H$_5$ClNOP (137.5)

calculated: 26.18% C; 3.64% H; 25.82% Cl; 10.18% N; 22.55% P; found: 26.3 % C; 3.6 % H; 25.5 % Cl; 9.7 % N; 21.1 % P.

3. Cyanomethyl-methylphosphinic acid chloride 313 g (1.5) of phosphorus pentachloride were added to 220.5 g (1.5 mol) of ethyl cyanomethyl-methylphosphinate in portions at 20°-25° C. with stirring and cooling. Stirring was continued, and the mixture was subsequently heated to reflux until no more waste gas could be detected. Phosphoryl chloride present in the reaction mixture was then distilled off under an aspirator vacuum. The residue was distilled at 0.067 kPa at a bath temperature of 140° C. by means of a thin-film evaporator to give 153 g of cyanomethyl-methylphosphinic acid chloride. This corresponds to a yield of 74% of theory.

I claim:

1. A compound of the formula I

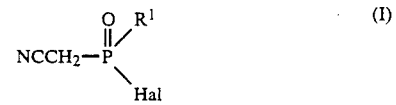

wherein R$^1$ represents Hal or C$_1$-C$_3$-alkyl and Hal represents a halogen having an atomic weight in the range from 35 to 80.

2. A compound according to claim 1, wherein Hal means chlorine.

3. A compound according to claim 1, wherein R$^1$ means methyl.

4. Cyanomethane phosphonic acid dichloride as a new compound according to claim 2.

5. Cyanomethyl-methylphosphinic acid chloride as a new compound according to claim 3.

6. A process for the production of compounds according to claim 1, which comprises reacting a compound of the formula II

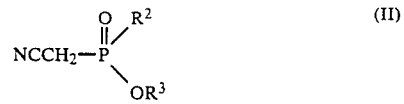

in which R$^2$ represents C$_1$-C$_3$-alkyl or OR$^3$ and R$^3$ represents C$_1$-C$_8$-alkyl, with an acid halide of the formula XHal$_2$ (III), wherein M represents SO, CO or PHal$_3$ and Hal represents a halogen having an atomic weight in the range of from 35 to 80, with the proviso that, where M is CO, the reaction is carried out in the presence of a catalyst conventional for the phosgenation of phosphonic acid diesters.

7. A process as claimed in claim 6, wherein in the acid halide X represents CO or SO and a catalyst is applied in an amount in the range of from 0.01 to 5%, referred to the weight of compound II.

8. A process as claimed in claim 7, wherein the amount is in the range of from 0.5 to 2% by weight.

9. A process as claimed in claim 6, wherein in the acid halide X represents CO or SO and the reaction is carried out at a temperature in the range of from 70° to 150° C.

10. A process as claimed in claim 9, which is carried out at a temperature in the range of from 80° to 110° C.

11. A process as claimed in claim 6, wherein in the acid halide X represents PHal$_3$ and the reaction is carried out at a temperature in the range of from −10° to +100° C.

12. A process as claimed in claim 11, which is carried out at a temperature in the range of from 20° to 80° C.

* * * * *